US006479425B1

(12) United States Patent
Stibrany et al.

(10) Patent No.: US 6,479,425 B1
(45) Date of Patent: Nov. 12, 2002

(54) LATE TRANSITION METAL COMPLEXES, THEIR USE AS CATALYSTS AND POLYMERS THEREFROM

(75) Inventors: Robert T. Stibrany, Long Valley; Smita Kacker, Clinton, both of NJ (US)

(73) Assignee: ExxonMobile Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/642,488

(22) Filed: Aug. 18, 2000

(51) Int. Cl.[7] .............................. B01J 31/18; C08F 4/44
(52) U.S. Cl. ....................... 502/165; 502/103; 502/117; 502/167; 526/161; 526/164; 526/172
(58) Field of Search ................................ 502/103, 117, 502/165, 167; 526/161, 172, 164

(56) References Cited

U.S. PATENT DOCUMENTS

| | | | |
|---|---|---|---|
| 3,558,520 A | 1/1971 | Kubicek et al. | ............. 252/429 |
| 3,703,561 A | 11/1972 | Kubicek et al. | ............. 260/683 |
| 5,369,073 A | 11/1994 | Sommazi et al. | ............ 502/162 |
| 5,556,823 A | 9/1996 | Sommazi et al. | ............ 502/165 |
| 5,880,241 A | 3/1999 | Brookhart et al. | ........... 526/348 |
| 6,037,297 A | 3/2000 | Stibrany et al. | ............. 502/155 |
| 6,103,658 A * | 8/2000 | Mackenzie et al. | .......... 502/126 |

FOREIGN PATENT DOCUMENTS

| | | | |
|---|---|---|---|
| EP | 0965600 | 12/1999 | |
| JP | 70040544 | 12/1970 | |
| WO | WO96/30421 | 3/1996 | ......... C08F/297/00 |
| WO | WO9630421 | 10/1996 | |
| WO | WO9806758 | 2/1998 | |
| WO | WO9930822 | 6/1999 | |
| WO | WO9955751 | 11/1999 | |

OTHER PUBLICATIONS

"Complexes of Copper with a Flexible Bis–benzimidazole Ligand," Gerald Bernardinelli, et al., CHIMIA 46(1992), pp. 155–158.

"Self–Assembly of DinuclearHelial and Nonhellical Complexes with Copper (I)," Stephane Ruttimann, et al., J Am. Chem. Soc. 1992, 114, pp. 4230–4237.

"Studies on Perchlorate Comlexes of CU(II) and Ag(I) with Substituted Benzimidazoles," N. Donappa, et al., Asian Journal of Chemistry, vol. 4(1992), pp. 879–885.

"Synthesis, Structure, and Reactivity of Model Complexes of Copper Nitrite Reductase," Luigi Casella, et al., Inorg. Chem., 1996, 35, pp. 1101–1113.

"Synthesis, Characterisation, Antifungal and Antibacterial Studies of Nickel(II) and Silver(I) Complexes of Tridentate Bis Benzimidazoles," P. C. Vyas, et al., Asian Journal of Chemistry, vol. 9, No. 2(1997), pp. 208–212.

"Preparation and Crystal Structure of the Unusual Double–Helical Copper(I) Complex Bis(2, 6–bis(1–methylbenzimidazol–2–yl)pyridine)dicopper(I) Naphthalene–1,5–disulfonate," Claude Piguet, et al., Inorg. Chem. 1989, 28, pp. 2920–2925.

"Copper Complexes of the "Tripod" Ligand Tris(2–benzimidazolymethyl)amine: Five–and Six–Coordinate Copper(II) Derivatives and Some Copper(I) Derivatives," Anthony W. Addison, et al., Inorganiz Chemistry, vol. 20, No. 1, 1981, pp. 103–110.

"Crystal structure of 1,3–bis(1–methylbenzimidazol–2–yl)–propane(acetonitrile)copper(I)hexafluorophosphate, $CU(C_{19}H_{20}N_4)(CH_3CN)(PF_6)$," G. Bernardinelli, Zeitschrift fur Kristallographie 203, 135–137(1993).

"New Ways for the Preparation of Heterocyclic Gold (III) Complexes": R. Usón, J. Vicente and M. T. Chicote, Department of Inorganic Chemistry, University of Zaragoza (Spain), Oct. 13, 1980; Jouranl of Organometallic Chemistry, 209 (1981) pp. 271–279; XP–00103111.

"Synthesis and Crystal Structure of Three–Coordinated Silver (I) and Copper (I) Complexes with $N_2P$ Binding Set Containing a Novel Ligand : 1,3,5–tris (benzimidazol–2–ylmethyl)benzene"; Wei–Yin Sun, Jin Xie, Yu–Hua Mei and Kai–Bei Yu; Jun. 14, 2000; The Royal Society of Chemistry and the Centre National de la Recherche Scientifique 2000; New J. Chem., 2000, 24, pp. 519–522; XP–001039628.

"Benzimidazol–2–ylcarbinols and Benzimidazol–2–yl Ketones; Novel Bifunctional Chelating Ligands for Copper"; Sergiu M. Gorun and Robert T. Stibrany; Alan R. Katritzky, Jarosalw J. Slawinski, Hassan Faid–Allah, and Frédéric Brunner; Inorg. Chem. 1996, 35, pp. 3–4; XP–001039629.

(List continued on next page.)

Primary Examiner—David W. Wu
Assistant Examiner—Caixia Lu
(74) Attorney, Agent, or Firm—Charles J. Brumlik

(57) ABSTRACT

The invention provides a novel metal complex which, when used with an activating cocatalyst, provides a novel catalyst composition. The invention also provides a polymerization method which utilizes the catalyst composition to produce polymers and copolymers containing polar monomer groups. More specifically, the invention comprises a composition comprising the formula $LMXZ_n$ wherein X is selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert. M is selected from the group consisting of Cu, Ag, and Au. L is a nitrogen-containing bidentate ligand having more than two nitrogen atoms. Z is a neutral coordinating ligand and n equals 0, 1, or 2.

10 Claims, No Drawings

OTHER PUBLICATIONS

"Preparation and Crystal Stuctures of Neutral and Cationic Copper (I) Mixed Ligand Complexes with Triphenylphosphane and Derivatives of Biimidazole"; S. de Souza Lemos, K. E. Bessler, and Schulz Lang; Z. anorg. Allg.Chem. 624(1998), pp. 701–707; XP–001039635.

Wideband Multiwavelength Erbium–Doped Fiber Ring Laser; Seung Kwan Kim, Moo Jung Chu, Dong Ho Lee, and Jae Geun Kim; Optical Communications Dept., Switching and Transmission Tech. Lab, Korea; XP–001035962.

Selective Oxidants for Organometallic Compounds Containing a Stabilising Anion of Highly Reactive Cations: $(3,5(CF_3)_2C_6H_3)_4Cp_2Fe^+$ and $(3,5(CF_e)_2C_6H_3)_4B^-)Cp_2*Fe^+$; Ivonne Chávez, et.al., Jan. 5, 2000; Journal of Organometallic Chemistry vol. 601 (2000), pp. 126–132.

* cited by examiner

LATE TRANSITION METAL COMPLEXES, THEIR USE AS CATALYSTS AND POLYMERS THEREFROM

FIELD OF THE INVENTION

The invention is directed towards a late transition metal polymerization catalyst complex and its use in forming polymers from olefins or polar monomers and copolymers from olefins and polar monomers.

BACKGROUND

Polymers and copolymers may be formed from olefinic monomers by using transition metal catalyst technology. Ziegler-Natta catalysts have been used for many years while in more recent years metallocene catalysts have been preferred in certain applications since the polyolefins produced via metallocene catalysis often possess superior properties. The most well-known metallocene technology employs catalysts containing early transition metal atoms such as Ti and Zr.

Even though polyolefins formed by such metallocene catalysts possess certain enhanced properties over polyolefins produced by conventional Ziegler-Natta catalysts, further improvements in properties such as wettability and adhesiveness may be possible. It is believed that including polar monomers in an olefinic polymer or copolymer would improve these, and possibly other, properties. Unfortunately, polar monomers tend to poison early transition metal catalysts.

Certain late transition metal complexes such as those containing palladium and nickel, are more forgiving when incorporating certain polar monomers. However, most of these catalyst compositions are costly and produce highly branched polymers (e.g., 85–150 branches/1000 carbon atoms). Also, the functionalities are not in the chain but at the ends of branches. Consequently, they are limited to polar monomer contents to about 15 mol % or less. Another disadvantage of these compositions is that they incorporate only a limited number of polar monomers such as alkyl acrylates and vinyl ketones.

Recently, novel late transition organometallic catalysts have been made to address the aforementioned problems. More specifically, U.S. Pat. No. 6,037,297 to Stibrany et al., herein incorporated by reference, details group 11 metal (Cu, Ag and Au) containing catalyst compositions having a pseudotetrahedral geometry that are useful in forming polymers and copolymers having hydrocarbyl polar functionality.

However, there is still a need to explore other group 11 metal complexes for use in polymerization processes. Ideally, these late transition metal complexes should be capable of forming olefinic polymers and copolymers containing polar monomers which are not highly branched, have polymer chain functionality and are capable of incorporating a wider variety of polar monomers.

SUMMARY

The instant invention provides a late transition metal complex which can be used with an activating cocatalyst to produce polymers and copolymers. Also, like the invention described in U.S. Pat. No. 6,037,297, the instant invention can be used to produce polymers and copolymers containing polar monomers.

In one embodiment, the invention is a composition having the formula $LMXZ_n$ wherein X is selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert. M is selected from the group consisting of Cu, Ag, and Au. L is a nitrogen-containing bidentate ligand with more than two nitrogen atoms. Z is a neutral coordinating ligand and n equals 0, 1, or 2.

In another embodiment, the invention is a catalyst composition comprising the reaction product of: a metal complex having the formula $LMXZ_n$, as described above, and an activating cocatalyst. This embodiment of the invention is particularly useful in polymerization chemistry.

In yet another embodiment, the invention provides a method for using the composition to produce polymers and copolymers which contain polar monomer units. The method includes contacting the monomers under polymerization conditions with a catalyst composition comprising a composition having the formula $LMXZ_n$, as defined above, and an activating cocatalyst. Optionally, an oxidizing agent may also be employed during this process.

These and other features, aspects and advantages of the present invention will become better understood with regard to the following description and appended claims.

DESCRIPTION

The invention relates to a novel metal complex which, when used with an activating cocatalyst, provides a novel catalyst composition. The invention also provides a polymerization method which utilizes the catalyst composition. Generally speaking, the method of the invention produces polymers and copolymers containing polar monomer groups.

In one embodiment, the invention comprises a composition comprising the formula $LMXZ_n$ wherein X is selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert; M is selected from the group consisting of Cu, Ag, and Au; L is a nitrogen-containing bidentate ligand with more than two nitrogen atoms; Z is a neutral coordinating ligand; wherein n equals 0, 1, or 2.

The geometric configuration of the metal complex of the instant invention can be either pseudotetrahedral or trigonal planar depending on the value of n (i.e., n can equal 0, 1 or 2). It should be appreciated by those skilled in the art that although the term "pseudotetrahedral" is used to describe the geometric structure of the metal complex, it does not exclude a pure "tetrahedral" geometrical arrangement. The prefix "pseudo" is used throughout the specification to most accurately describe the non-limiting embodiments described herein. Similarly, the term "trigonal planar" should be understood by those skilled in the art to also include geometric configurations which are approximately trigonal planar.

When the metal composition is reacted with an activating cocatalyst such as methyl alumoxane (a.k.a., "MAO") a catalyst composition is created. Thus, in another embodiment, the invention is a catalyst composition comprising the reaction product of: (a) A metal complex having the formula $LMXZ_n$ wherein X is selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert; M is selected from the group consisting of Cu, Ag, and Au; L is a nitrogen-containing bidentate ligand with more than two nitrogen atoms; Z is a neutral coordinating ligand; where n equals 0, 1, or 2; and (b) an activating cocatalyst.

Furthermore, by controlling the temperature, catalyst loading, ligand structure, and residence time, product selectivity can be adjusted to produce individual polymers and copolymers with high selectivity. Hence, in yet another embodiment, the invention provides a method for producing polymers and copolymers.

Ideally, Z is weakly coordinating and sufficiently labile to allow activation of the catalyst. In a preferred embodiment composition, for each occurrence of Z, each Z is independently selected from the group consisting of diethylether, tetrahydrofuran, acetonitrile, benzonitrile, dioxane, acetone, 2-butanone, phenylisocyanate, ethylene, carbon monoxide, 1-hexene, and norbornene.

In another preferred embodiment of this invention is a complex having the formula $LMXZ_n$, as described above, where L is a nitrogen-containing bidentate ligand represented by the formula:

[ARA'] and [AA'], wherein A and A' are independently selected from the group consisting of

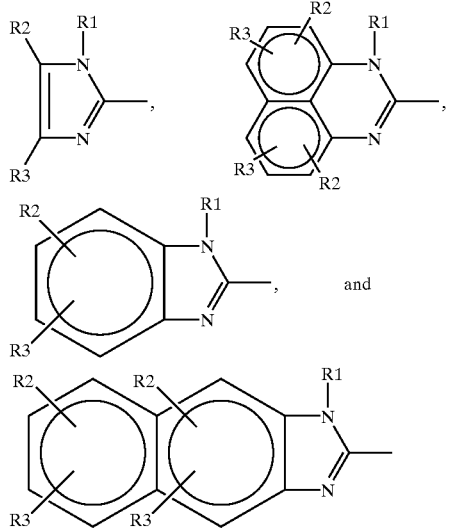

wherein R1 is independently selected from the group consisting of hydrogen, $C_1$ through $C_{12}$ straight chain or branched alkyl, $C_3$ through $C_{12}$ cycloalkyl, aryl, and trifluoroethane;

R2 and R3 are independently selected from the group consisting of hydrogen, $C_1$ through $C_{12}$ straight chain or branched alkyl, $C_3$ through $C_{12}$ cycloalkyl, $C_1$ through $C_{12}$ alkoxy, F, Cl, $SO_3$, $C_1$ through $C_{12}$ perfluoroalkyl, and $N(CH_3)_2$;

R is selected from the group consisting of non-substituted $C_1$ through $C_{12}$ alkyl, $C_3$ through $C_{12}$ cycloalkyl; methoxy; amino; halo; $C_1$ through $C_{12}$ haloalkyl substituted alkyl; cycloalkyl of up to 12 carbon atoms, $C_1$–$C_{40}$ aryl; and $C_1$–$C_{40}$ alkylaryl.

X is selected from the group consisting of halogens, hydride, triflate, acetate, trifluoroacetate, perfluorotetraphenylborate, tetrafluoroborate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, and any other moiety into which a monomer can insert such as an atom, or group of atoms, covalently or inonically bonded to M; Z is a neutral coordinating ligand; where n equals 0, 1, or 2. In a preferred embodiment, for each occurrence of Z, each Z is independently selected from the group consisting of diethylether, tetrahydrofuran, acetonitrile, benzonitrile, dioxane, acetone, 2-butanone, phenylisocyanate, ethylene, carbon monoxide, 1-hexene, and norbornene.

Accordingly, some of the ligands of the present invention have the following structures:

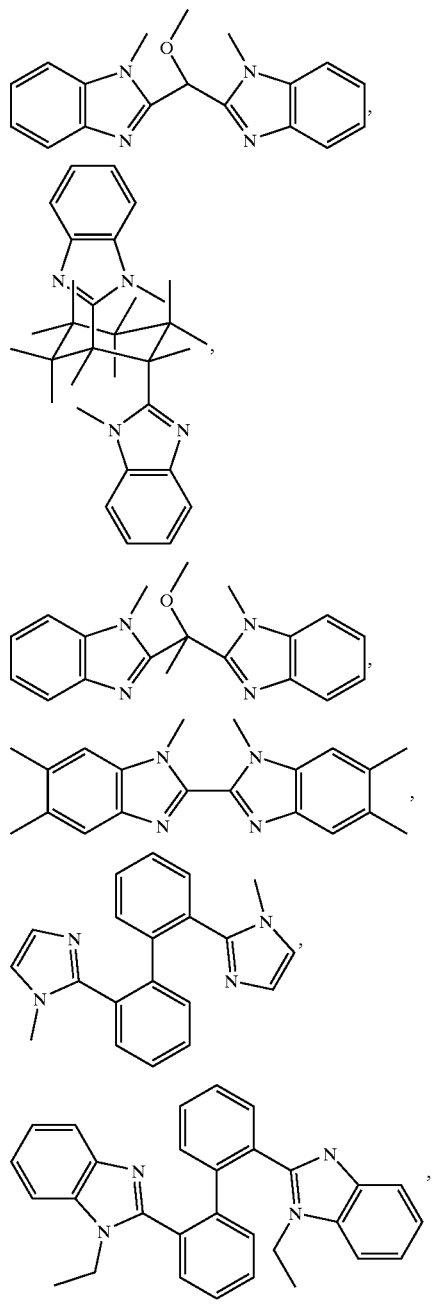

-continued

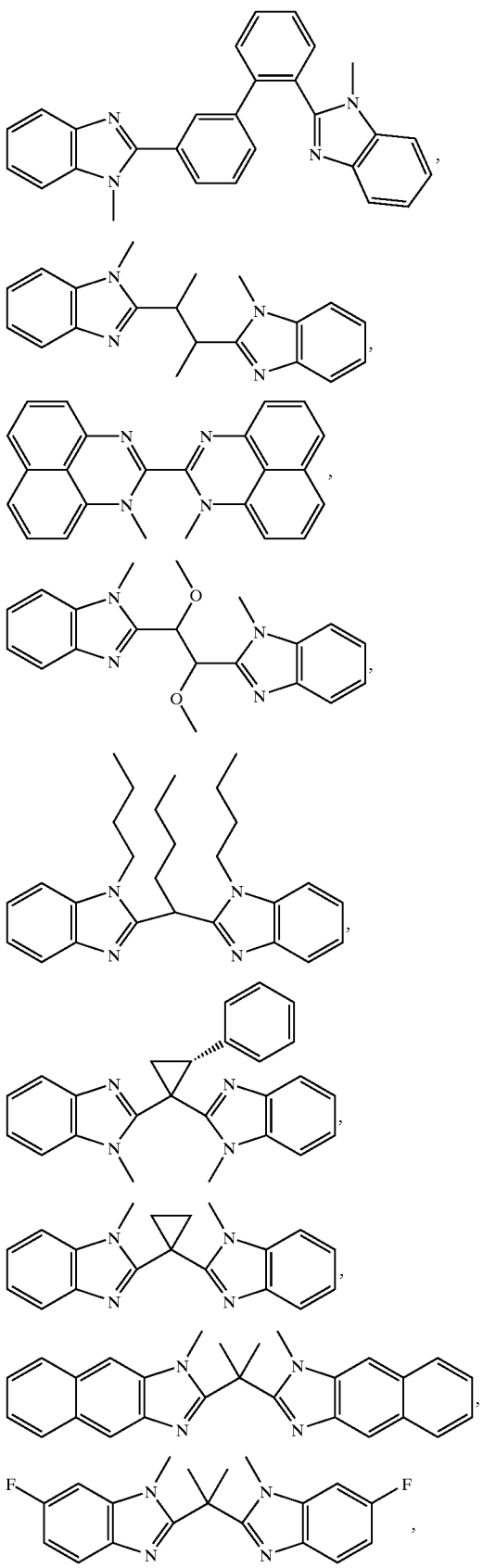

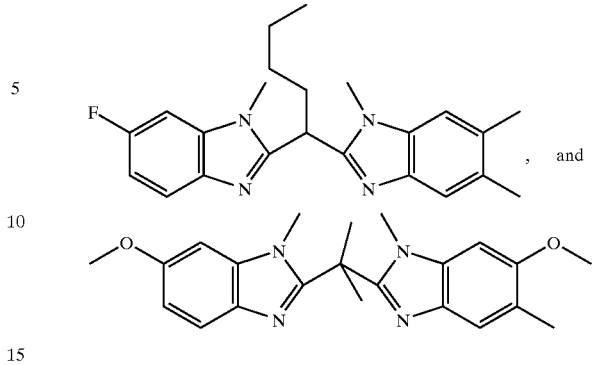

and. For compactness, some bonds are shown without termination; these bonds are terminated by methyl groups.

Cu is preferred for M. Among the options for X, halogens are preferred. Suitable non-halide options for X include, but are not limited to, triflate, trifluoroacetate, perfluorotetraphenyl borate, or tetrafluoro borate, hydride, alkyl groups or any other ligand into which a monomer can insert such as an atom, or group of atoms, covalently or inonically bonded to M.

Among the metal complexes of the present invention, particularly preferred embodiments are those having the 2,2'-bis[2-(1-alkylbenzimidazol-2-yl)]biphenyl, where the alkyl group is from $C_1$–$C_{20}$, and for X is chloride.

Generally, the 2,2'-bis[2-(1-alkylbenzimidazol-2-yl)]biphenyl ligands having copper as the metal and chlorine as X, and $C_1$–$C_{20}$ as $R_1$, have the structure

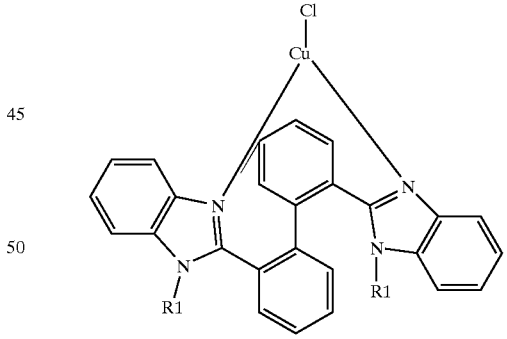

Preferred embodiments of specific metal complexes include, but are not limited to, the following:

Preferred embodiments of specific metal complexes include, but are not limited to, the following:

[(2,2'-bis[2-(1-ethylbenzimidazol-2-yl)]biphenyl)(acetonitrile)copper(I)](tetrafluoroborate)

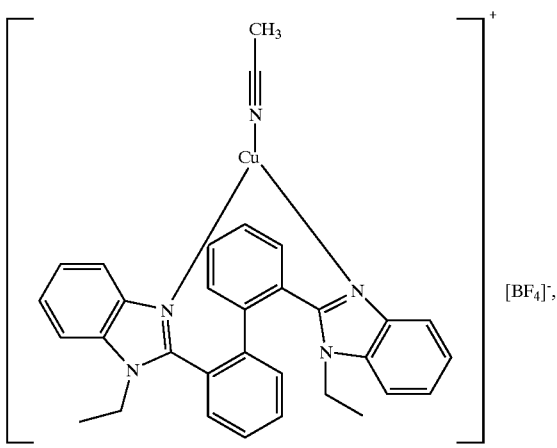

and (2,2'-bis[2-(1-ethylbenzimidazol-2-yl)]biphenyl)copper (I)chloride

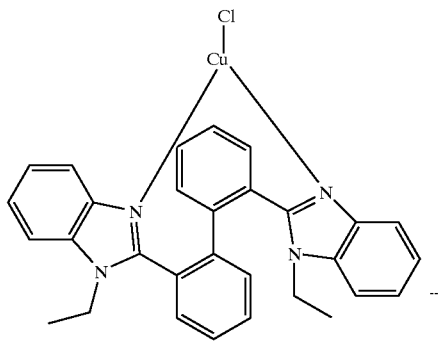

Advantageously, the catalysts of the present invention are not poisoned by compounds containing hydrocarbyl polar functional groups when used in the formation of polymers and copolymers synthesized all or in part from olefinic monomers. As such, the catalysts of the present invention are useful in preparing polymers and copolymers formed from olefinic monomers, such as polyethylene; polymers and copolymers formed from monomers containing hydrocarbyl polar functional groups such as poly(methyl methacrylate); and copolymers derived from olefins and monomers containing hydrocarbyl polar functional groups such as poly (ethylene-co-methyl methacrylate).

The activating cocatalysts used in conjunction with the metal complex defined above include, but are not limited to, aluminum compounds containing an Al—O bond such as the alkylalumoxanes such as methylalumoxane ("MAO"), isobutyl modified methylalumoxane ("MMAO"); "dry" [i.e., sovent free and $Me_3Al$ ("TMA") free] MAO; aluminum alkyls; aluminum halides; alkylaluminum halides; Lewis acids other than any of the foregoing list; and mixtures of the foregoing can also be used in conjunction with alkylating agents, such as methyl magnesium chloride and methyl lithium. Examples of such Lewis acids are those compounds corresponding to the formula: $R''''_3B$, or $R_3''''Al$ wherein $R''''$ independently each occurrence is selected from hydrogen, silyl, hydrocarbyl, halohydrocarbyl, alkoxide, aryloxide, amide or combinations thereof, said $R''''$ having up to 30 nonhydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Other examples of such cocatalysts include salts of group 13 element complexes. These and other examples of suitable cocatalysts and their use in organometallic polymerization are discussed in U.S. Pat. No. 5,198,401 and PCT patent documents PCT/US97/10418 and PCT/US96/09764, all incorporated by reference herein.

Preferred activating cocatalysts include trimethylaluminum, triisobutylaluminum, methylalumoxane, alkyl modified alumoxanes, "dry" alumoxanes, chlorodiethyaluminum, dichloroethylaluminum, triethylboron, trimethylboron, triphenylboron and halogenated, especially fluorinated, triaryl boron and aluminum compounds, carboranes and halogenated carboranes.

Most highly preferred activating cocatalysts include triethylaluminum, methylalumoxane, and fluoro-substituted aryl boranes and borates such as tris(4-fluorophenyl)boron, tris(2,4-difluorophenylboron), tris(3,5-bis(trifluoromethylphenyl)boron, tris(pentafluorophenyl)boron, pentafluorophenyl-diphenyl boron, and bis(pentafluorophenyl)phenylboron and tetrakis(pentafluorophenyl)borate. Such fluoro-substituted arylboranes may be readily synthesized according to techniques such as those disclosed in Marks, et al., J. Am. Chem. Soc., 113, 3623–3625 (1991). Fluorinated tetraaryl borates or aluminates and perfluoro tetranapthyl borates or aluminates, are also well known in the art.

The catalyst can be utilized by forming the metal complex $LMXZ_n$, as defined above, and where required combining the activating cocatalyst with the same in a diluent. Optionally, an oxidizing agent may also be utilized in conjunction with the cocatalyst. Oxidizing agents may include, but are not limited to: $NOBF_4$; 1,4-benzoquinone; tetrachloro-1,4-benzoquinone; $AgClO_4$; $Ag(C_6F_5)_4B$; ferricinium $(C_6F_5)_4B$; $(3,5(CF_3)_2(C_6H_4)B)Cp_2Fe^+$; and $(3,5(CF_3)_2(C_6H_4)B)Cp_2{}^*Fe^+$. The preparation may be conducted in the presence of one or more addition polymerizable monomers, if desired. Preferably, the catalysts are prepared at a temperature within the range from $-100°$ C. to $300°$ C., preferably $0°$ C. to $250°$ C., most preferably $0°$ C. to $100°$ C. Suitable solvents include liquid or supercritical gases such as $CO_2$, straight and branched-chain hydrocarbons such as isobutane, butane, pentane, hexane, heptane, octane, and mixtures thereof, cyclic and alicyclic hydrocarbons such as cyclohexane, cycloheptane, methylcyclohexane, methylcycloheptane, halogenated hydrocarbons such as chlorobenzene, and dichlorobenzene perfluorinated $C_{4-10}$ alkanes and aromatic and alkyl-substituted aromatic compounds such as benzene, toluene and xylene. Suitable solvents also include liquid olefins which may act as monomers or comonomers including ethylene, propylene, butadiene, 1-hexene, 3-methyl-1-pentene, 4-methyl-1-pentene, 1-octene, 1-decene, and 4-vinycylohexane, (including all isomers alone or in mixtures). Other solvents include anisole, methylchloride, methylene chloride, 2-pyrrolidone and N-methylpyrrolidone. Preferred solvents are aliphatic hydrocarbons and aromatic hydrocarbon, such as toluene.

When an activating cocatalyst is used to form the catalyst composition, the equivalent ratio of metal complex to activating cocatalyst is preferably in a range from 1:0.5 to 1:$10^4$, more preferably from 1:0.75 to 1:$10^3$. In most polymerization reactions the equivalent ratio of catalyst:polymerizable compound employed is from $10^{-12}$: to $10^{-1}$:1, more preferably from $10^{-9}$:1 to $10^{-4}$:1.

Olefinic monomers useful in the forming homopolymers and copolymers with the catalyst of the invention include, but are not limited to, ethylenically unsaturated monomers, nonconjugated dienes, and oligomers, and higher molecular weight, vinyl-terminated macromers. Examples include $C_{2-20}$ olefins, vinylcyclohexane, tetrafluoroethylene, and mixtures thereof. Preferred monomers include the $C_{2-10}$ α-olefins especially ethylene, propylene, isobutylene, 1-butene, 1-hexene, 4-methyl-1-pentene, and 1-octene or mixtures of the same.

Monomers having hydrocarbyl polar functional groups useful in forming homo and copolymers with the catalyst of the invention, are vinyl ether and $C_1$ to $C_{20}$ alkyl vinyl ethers such as n-butyl vinyl ether, acrylates, such as $C_1$ to $C_{24}$, or alkyl acrylates such as t-butyl acrylate, and lauryl acrylate, as well as methacrylates such as methyl methacrylate.

In general, the polymerization may be accomplished at conditions well known in the prior art for Ziegler-Natta or Kaminsky-Sinn type polymerization reactions, that is, temperatures from −100° C. to 250° C. preferably 0° C. to 250° C., and pressures from atmospheric to 2000 atmospheres (200 Mpa). Suitable polymerization conditions include those known to be useful for metallocene catalyst when activated by aluminum or boron-activated compounds. Suspension, solution, slurry, gas phase or other process condition may be employed if desired. The catalyst may be supported and such supported catalyst may be employed in the polymerizations of this invention. Preferred supports include alumina, silica, polymeric supports and meso-porous materials.

The polymerization typically will be conducted in the presence of a solvent. Suitable solvents include those previously described as useful in the preparation of the catalyst. Indeed, the polymerization may be conducted in the same solvent used in preparing the catalyst. Optionally, of course, the catalyst may be separately prepared in one solvent and used in another.

The polymerization will be conducted for a time sufficient to form the polymer and the polymer is recovered by techniques well known in the art and illustrated in the following non-limiting examples which help to further described the invention.

EXAMPLE 1

Preparation of [Cu(diEtBBIL)(ACN)](BF$_4$)

In an argon glovebox a colorless solution of 35 mg (0.11 mmol) of Cu(ACN)$_4$(BP$_4$) in 8 mL of acetonitrile was prepared. Then, 50 mg (0.1 1 mmol) of diEtBBIL was added to the solution and thoroughly mixed. The flask containing the colorless solution was then placed in a sealed jar containing diethylether to allow vapor diffusion. After one day colorless crystals of rac-[(2,2'-bis[2-(1-ethylbenzimidazol-2-yl)]biphenyl)(acetonitrile)copper(I)] (tetrafluoroborate) were obtained. $^1$H NMR (CDCl$_3$): δ=7.65(d, J=6,7 Hz, 2H), 7.54(dd, J=7.8 Hz, J=17.9 Hz, 4H), 7.33(m, 8H), 6.93(d, J=7,4 Hz, 2H), 4.47(dm, J=40.3 Hz, 4H), 2.15(s, 3H), 1.66(t, J=6.8 Hz, 6H). X-ray crystallographic data: monoclinic, P2(1), Z=4, a=16.952(3), b=15.527(3), c=12.946(2), α=90, β=111.33(3), γ=90, V=3174.15.

EXAMPLE 2

Preparation of Cu(I)(diEtBBIL)Cl by Reduction

A 100 mg quantity of 10μ copper powder was placed in a 100 mL round bottom flask with a side arm. Then, 2 mL of triethylorthoformate and 20 mL of acetonitrile were added to the flask. The flask was fitted with bubbler and was degassed under a continuous flow of nitrogen. Then, 33 mg (0.19 mmol) of CuCl$_2$.2 H$_2$O was added to the stirring mixture under a positive flow of nitrogen to give a green solution. Then, 170 mg (0.38 mmol) of diEtBBIL was added to the flask to give a yellow solution. The mixture was stirred under nitrogen for more than 72 hours. The flask containing the colorless solution and remaining solid was then filtered to give a colorless filtrate. The solvent was removed under a flow of nitrogen to give a white solid. The solid was placed under high vacuum an additional hour to give 144 mg of white (2,2'-bis[2-(1-ethylbenzimidazol-2-yl)]biphenyl) copper(I)chloride. $^1$H NMR (CDCl$_3$): δ=8.08(m, 2H), 7.69 (m, 1), 7.53(m, 3H), 7.27(m, 6H), 6.95(dm, 4H), 4.38(dm, 4H), 1.58(m, 3H), 1.90(m, 3H).

EXAMPLE 3

Preparation of Polyethylene Using [Cu(I) (diEtBBIL)(ACN)](BF$_4$)

A 32.1 mg (0.051 mmol) quantity of Cu(diEtBBIL)(MeCN))BF$_4$ was weighed out in a glass liner under argon. Then, 30 mL of toluene was added to the liner, followed by 2.0 g of 30 wt. % MAO (0.010 mol) resulting in a pale yellow slurry. The liner was placed in a 300 mL Parr reactor which was sealed, pressurized with ethylene and heated to 80° C. The reaction was run for 15 hours at 720 psig. At the end of this time period, the reactor was cooled, vented and quenched with 5 mL of methanol. Then the polymer was precipitated out in 150 mL of acidic methanol (10%). The polymer was isolated by filtration and dried under vacuum at 50° C. for a day. Yield: 0.8 g. T$_m$: 142° C. (second heat). $^{13}$C NMR (ppm, 125° C. tetrachloroethane): 29.5 (s, —CH$_2$—CH$_2$—); no evidence of end groups and branch points up to the detection limits of about one carbon per 500–1000 carbons.

EXAMPLE 4

Preparation of Poly(t-butyl acrylate) Using [Cu(I) (diEtBBIL)(ACN)](BF$_4$)

A 32.1 mg (0.051 mmol) quantity of Cu(diEtBBIL)(MeCN))BF$_4$ was added to a 100 mL round-bottomed flask in an argon glovebox. 10 mL of toluene was added to the flask, followed by 1.02 g of 30 wt. % MAO (5.3 mmol) resulting in an yellow slurry. 5.9 g of t-butyl acrylate (freshly distilled from CaCl$_2$ and stabilized with 300 ppm of phenathiazine) was added to the slurry. The slurry was allowed to stir at room temperature for 18 hours in the dark. At the end of this time period, the reaction was quenched with 5 mL of methanol and then the polymer was precipitated out in 150 mL of acidic methanol (10%). The polymer was isolated by filtration and dried under vacuum at 40° C. for a day. Yield: 14%. $^{13}$C NMR (ppm, CDCl$_3$): 28.2 (s, —CH$_2$—CH(COOC(CH$_3$)$_3$)—), 34.3–37.6 (m, —CH$_2$—CH(COOC(CH$_3$)$_3$)—), 42–43.5 (m, —CH$_2$—CH(COOC(CH$_3$)$_3$)—), 80.5 (m, —CH$_2$—CH(COOC(CH$_3$)$_3$)—), 173.2–174.1 (m, —CH$_2$—CH(COOC(CH$_3$)$_3$)—), 39%rr, 47% mr, 14% mm (by integration of methine peak).

EXAMPLE 5

Preparation of Polyethylene Using [Cu(I) (diEtBBIL)(ACN)](BF$_4$)

The polymerization was run using a mixture prepared by dissolving 21.1 mg (0.033 mmol) of [Cu(diEtBBIL)(ACN)]

(BF$_4$) in 80 ml of toluene to give a colorless solution. This was followed by the addition of 100 mg of NOBF$_4$ (0.85 mmol) maintaining a colorless solution. This was followed by the addition of 1.5 ml of 30% MAO to give an intense yellow solution. The Parr reactor was pressurized with 550 psig of ethylene and heated to 80° C. and maintained at 80° C. for 20.75 hours during which the pressure dropped from 560 psig to 540 psig. The polymerization mixture was cooled and quenched with methanol to give 31 mg of solid polyethylene upon workup.

EXAMPLE 6

Preparation of Poly(t-butyl acrylate-ethylene)

A 24.1 mg (0.045 mmol) quantity of Cu(diEtBBIL)Cl was weighed out in a glass liner under argon. 30 mL of toluene was added to the liner, followed by 1.98 g of 30 wt. % MAO (0.010 mol) resulting in a pale yellow slurry. Next, 10.7 grams of t-butyl acrylate (t-butyl acrylate was distilled from CaCl$_2$, degassed and taken into the glove box, then approximately 100 ppm phenathiazine was added) was added to the slurry. The liner was placed in a 300 mL Parr reactor which was sealed, pressurized with ethylene and heated to 80° C. The reaction was run for 17 hours at 840 psig. At the end of this time period, the reactor was cooled, vented and quenched with 5 mL of methanol and then the polymer was precipitated out in 300 mL of acidic methanol (10%). The polymer was isolated by filtration and dried under vacuum at 60° C. for a day. The yield was 4.5 g. The polymer was extracted in THF in a soxhlet extractor to remove any catalyst residue and characterized.

The composition of the copolymers was determined by $^{13}$C-NMR in CDCl$_3$. The acrylate ester content was calculated by averaging the integral values for the acrylate carbonyl and quaternary carbon of t-butyl group. Ethylene content is then obtained by correcting the total aliphatic integral for the t-butyl acrylate integration. Furthermore, acrylate-centered traits were quantified by integration of three clusters of methine resonances: EAE: 46.5, EAA/AAE: 44.2, AAA: 42.2 ppm. The copolymer was found to have 76 mol % t-butyl acrylate with EAE:EAA/AAE:AAA= 8:38:53.

The foregoing examples clearly demonstrate that the novel composition of the instant invention can be used as an effective polymerization catalyst to make polymers and copolymers including copolymers having polar functionality. More specifically, the examples show how polar monomers can be readily polymerized without poisoning the catalyst. Also, the chain, as opposed to the branches, contain a significant quantity of the polar monomer(s). Furthermore, the polymers formed are not highly branched. Additionally, the examples show that the polymers formed have a high percent of polar monomer content (e.g., greater than about 15 mol %). Finally, there are a variety of polar monomers which may be incorporated into the olefinic polymer and copolymer products. These features overcome the disadvantages of the most organometallic catalyst technology used today as discussed above in the background section.

What is claimed is:

1. A catalyst composition comprising the reaction product of:
    (a) A metal complex having the formula LMXZ$_n$ wherein X is selected from the group consisting of halides, hydride, triflate, acetates, borates, C$_1$ through C$_{12}$ alkyl, C$_1$ through C$_{12}$ alkoxy, C$_3$ through C$_{12}$ cycloalkyl, C$_3$ through C$_{12}$ cycloalkoxy, aryl, thiolates, carbon monoxide, cyanate, olefins, and any other moiety into which a monomer can insert; M is selected from the group consisting of Cu, Ag, and Au; L is a nitrogen-containing bidentate ligand having more than two nitrogen atoms; Z is a neutral coordinating ligand; wherein n equals 1 or 2; and (b) an activating cocatalyst.

2. The composition according to claim 1 wherein M is Cu.

3. The composition according to claim 1 wherein for each occurrence of Z, each Z is independently selected from the group consisting of diethylether, tetrahydrofuran, acetonitrile, benzonitrile, dioxane, acetone, 2-butanone, phenylisocyanate, ethylene, carbon monoxide, 1-hexene, and norbornene.

4. The composition according to claim 1 wherein X is hydride.

5. The composition according to claim 1 wherein X is triflate.

6. A catalyst composition comprising the reaction product of:
    (a) A metal complex having the formula LMXZ$_n$ wherein X is selected from the group consisting of halides, hydride, triflate, acetates, borates, C$_1$ through C$_{12}$ alkyl, C$_1$ through C$_{12}$ alkoxy, C$_3$ through C$_{12}$ cycloalkyl, C$_3$ through C$_{12}$ cycloalkoxy, aryl, thiolates, carbon monoxide, cyanate, olefins, and any other moiety into which a monomer can insert; M is selected from the group consisting of Cu, Ag, and Au; L is a nitrogen-containing bidentate ligand having more than two nitrogen atoms; Z is a neutral coordinating ligand; wherein n equals 0, 1, or 2; and (b) methyl alumoxane.

7. The composition according to claim 6 wherein M is Cu.

8. The composition according to claim 6 wherein for each occurrence of Z, each Z is independently selected from the group consisting of diethylether, tetrahydrofuran, acetonitrile, benzonitrile, dioxane, acetone, 2-butanone, phenylisocyanate, ethylene, carbon monoxide, 1-hexene, and norbornene.

9. The composition according to claim 6 wherein the X is hydride.

10. The composition according to claim 6 wherein the X is triflate.

* * * * *